US00PP31750P2

(12) United States Plant Patent
Malinowski et al.

(10) Patent No.: US PP31,750 P2
(45) Date of Patent: May 12, 2020

(54) ***HIBISCUS* PLANT NAMED '15719 GRW'**

(50) Latin Name: *Hibiscus hybrid (L.)*
Varietal Denomination: 15719 GRW

(71) Applicant: The Texas A&M University System, College Station, TX (US)

(72) Inventors: Dariusz P. Malinowski, Vernon, TX (US); William E. Pinchak, Vernon, TX (US); R. Steve Brown, Vernon, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 16/501,696

(22) Filed: May 22, 2019

(51) Int. Cl.
*A01H 5/02* (2018.01)
*A01H 6/60* (2018.01)

(52) U.S. Cl.
USPC ..... Plt./257

(58) Field of Classification Search
USPC ..... Plt./257
CPC ..... A01H 5/02; A01H 6/60
See application file for complete search history.

(56) References Cited

PUBLICATIONS

U.S. Appl. No. 16/501,691, filed May 22, 2019, Malinowski et al.
U.S. Appl. No. 16/501,698, filed May 22, 2019, Malinowski et al.
U.S. Appl. No. 16/501,694, filed May 22, 2019, Malinowski et al.
U.S. Appl. No. 16/501,693, filed May 22, 2019, Malinowski et al.
U.S. Appl. No. 16/501,695, filed May 22, 2019, Malinowski et al.
U.S. Appl. No. 16/501,692, filed May 22, 2019, Malinowski et al.
U.S. Appl. No. 16/501,697, filed May 22, 2019, Malinowski et al.

*Primary Examiner* — Annette H Para
(74) *Attorney, Agent, or Firm* — Dentons US LLP

(57) ABSTRACT

'15719 GRW' is a new and distinct hardy herbaceous *Hibiscus* hybrid with novel characteristics that include upright branched stems, numerous, outward-facing, very light purplish-blue flowers, which can intensify to very pale purplish blue in response to high UV radiation, with a dark-red eye with an external halo of vivid red, a prolonged blooming season, and hastate, trilobed leaves.

4 Drawing Sheets

Latin name of the genus and species of the plant claimed: *Hibiscus* hybrid (L.).

Cultivar denomination: '15719 GRW'.

BACKGROUND OF THE INVENTION

The invention relates to the new and distinct *hibiscus* plant '15719 GRW'. '15719 GRW' was generated from a cross performed on Jul. 22, 2014 near Vernon, Tex. between '12078-5' (pod parent, unpatented) and '14054-3M' (pollen parent, unpatented). The pedigrees of each parent reflect a complex mixture of *hibiscus* species that include, for example, *H. mocheutos, H. coccineus, H. militaris*, or *H. dasycalyx*. The seed from this cross was harvested on Sep. 7, 2014 and the '15719 GRW' seedling was selected in the summer of 2015. '15719 GRW' was first asexually propagated near Vernon, Tex. in 2016 by stem tip cuttings. The resulting as well as subsequent asexually propagated plants have been stable and true to type throughout successive generations.

SUMMARY OF THE INVENTION

'15719 GRW' differs from its parents and all other known hardy herbaceous *hibiscus* plants. The following are the most outstanding and distinguishing characteristics of '15719 GRW': (1) it is a hardy perennial with dense branching and a relatively compact growth habit; (2) it blooms profusely over a prolonged season; and (3) its flowers exhibit a very light purplish-blue (RHS 100C) background, which can intensify in response to high UV radiation (very pale purplish blue, RHS 101D), and a center eye that is dark red (RHS 59A) with an external halo of vivid red (RHS 57A).

'15719 GRW' plants can be readily and unambiguously distinguished from those of its parents. '15719 GRW' plants exhibit very light purplish-blue (RHS 100C) flowers that have an average diameter of 15 cm, petals that have waved edges and do not overlap, and hastate, trilobed leaves. Whereas, '12078-5' plants (pod parent) exhibit light purplish blue (RHS 95D) to very pale purplish blue (RHS 97C) flowers that have an average diameter of 10 cm and lobed leaves; and '14054-3M' plants (pollen parent) exhibit very pale purple (RHS 69B) flowers that have an average diameter of 16 cm and hastate leaves.

'15714-1N' (U.S. patent application Ser. No. 16/501,698) is the *hibiscus* plant that exhibits flowers that are colored most similarly to those of '15719 GRW'. Nonetheless, plants of '15719 GRW' and '15714-1N' can also be readily and unambiguously distinguished from one another at least based upon flower shape, petal shape, and growth habit. The petals of '15719 GRW' are not cupped and do not overlap; whereas, the petals of '15714-1N' are cupped and overlap. Also, plants of '15719 GRW' display a growth habit that is less compact than plants of '15714-1N'.

BRIEF DESCRIPTION OF THE DRAWINGS

'15719 GRW' is illustrated by the accompanying photographs, which show the plant's form, foliage, flowers, and leaves. The colors shown are as true as can be reasonably obtained by conventional photographic procedures.

DETAILED BOTANICAL DESCRIPTION

Figure 1:
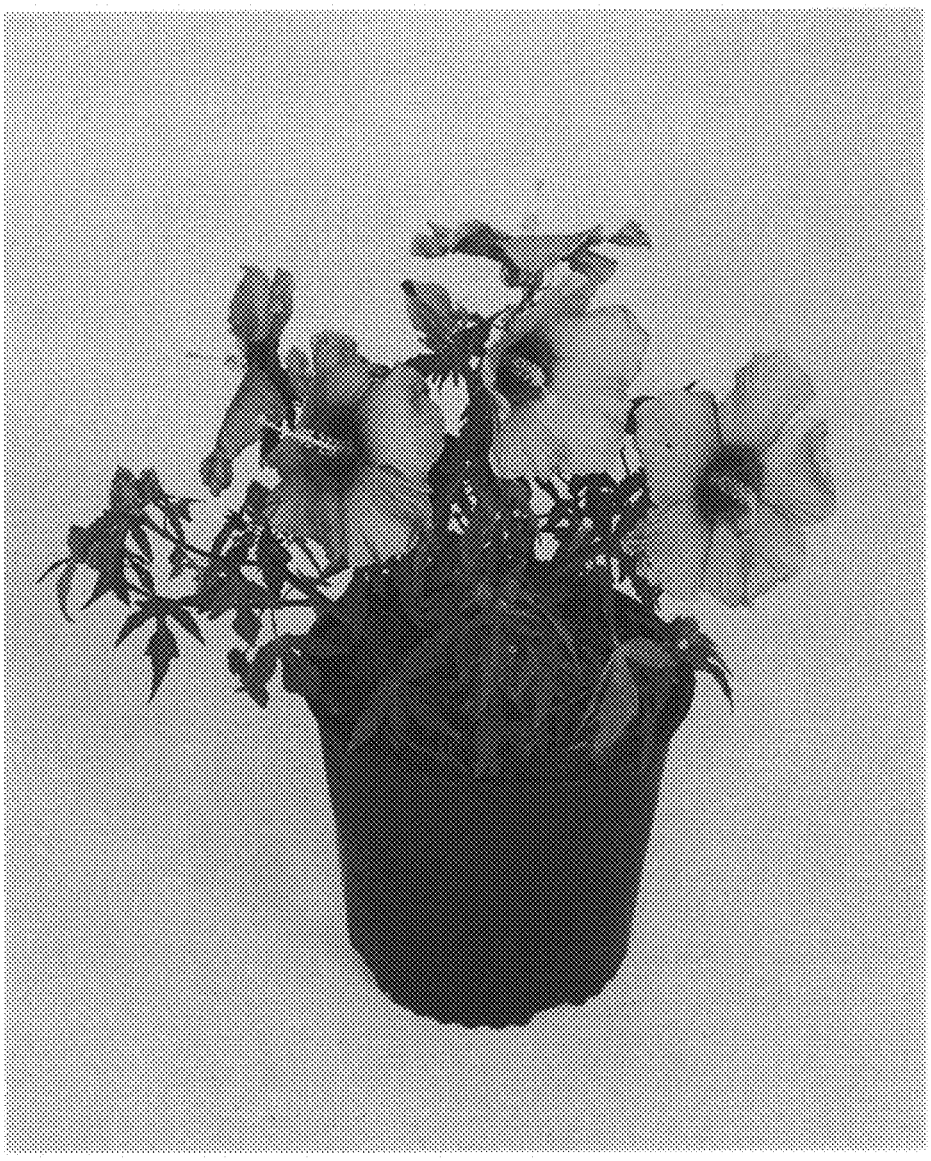
FIG. 1—Shows a 6-week-old '15719 GRW' plant in a container.
Figure 2:
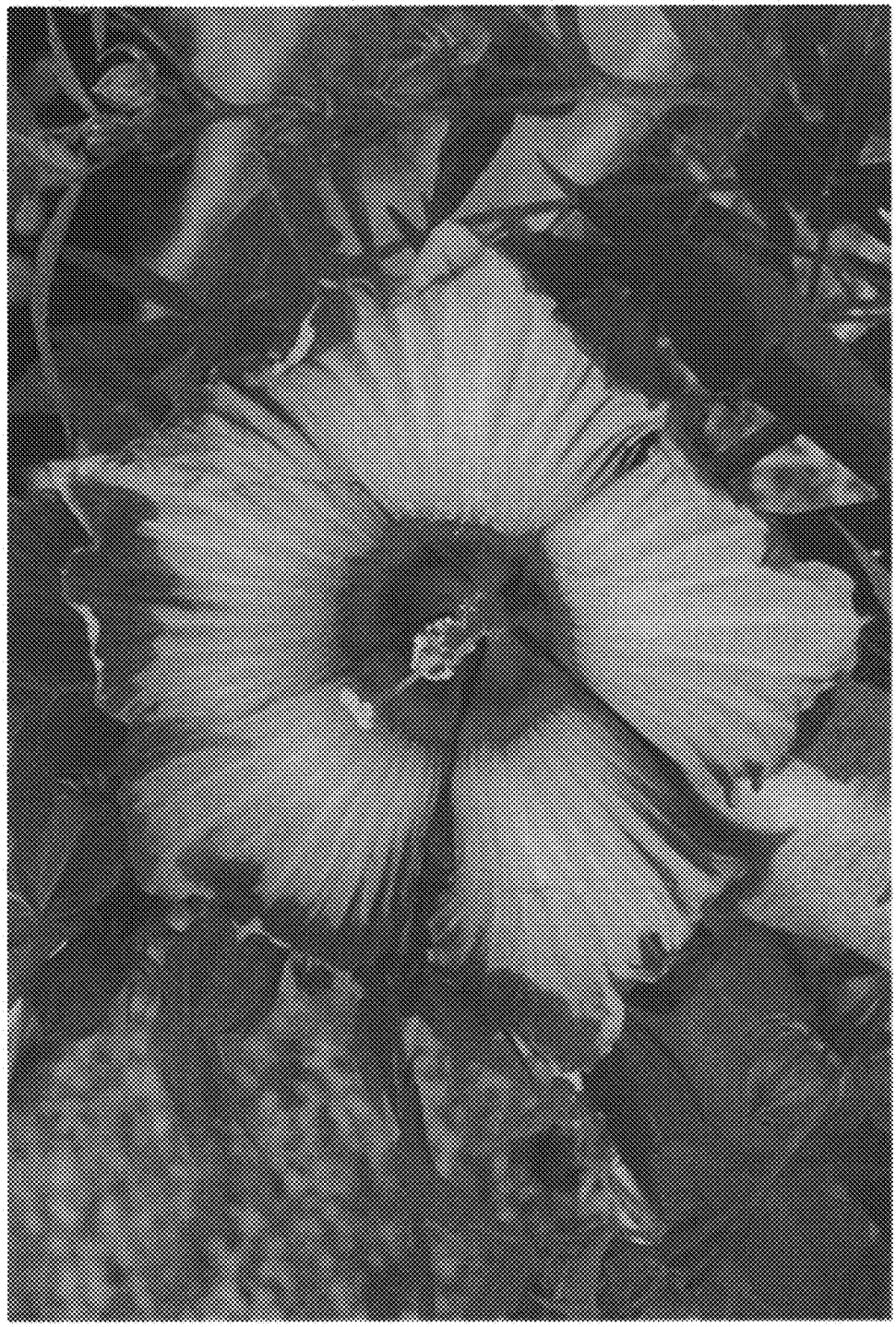
FIG. 2—Shows a '15719 GRW' flower as seen looking slightly askew from the adaxial surface of the petals on a 2-year-old plant.
Figure 3:
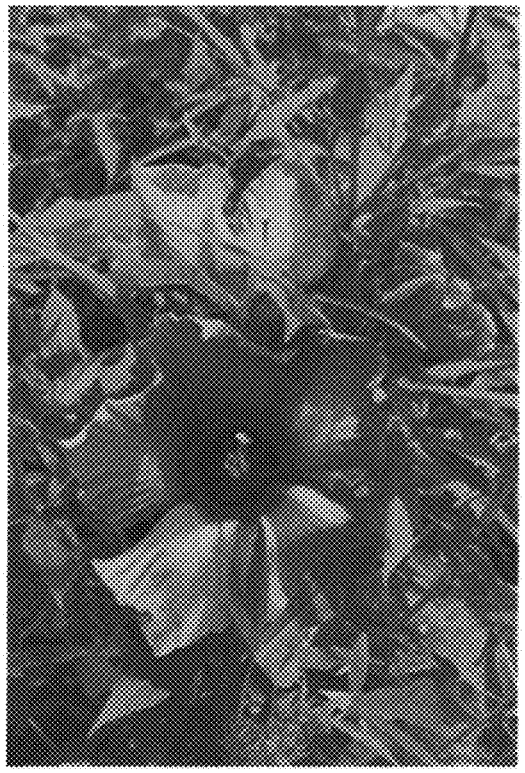
FIG. 3—Shows '15719 GRW' flowers, including one seen looking directly at the adaxial surface of the petals on a 2-year old plant.
Figure 4:
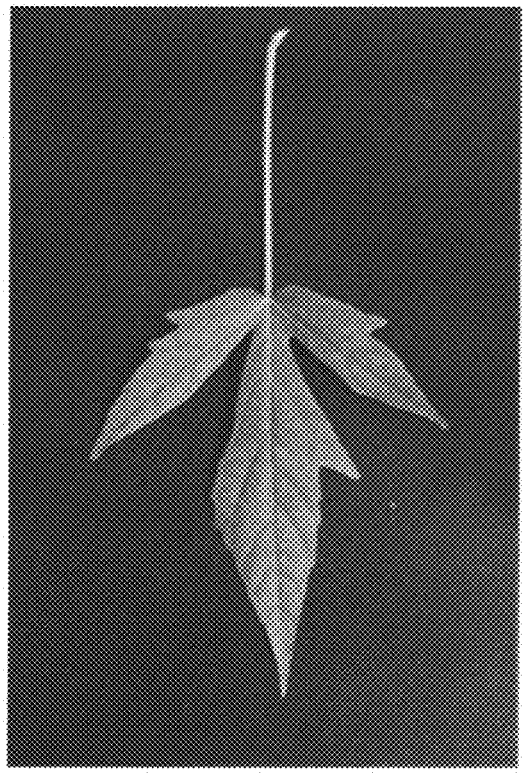
FIG. 4—Shows a '15719 GRW' leaf.

The following detailed description sets forth the distinctive characteristics of '15719 GRW'. The detailed description was obtained using two-year-old plants grown in loamy sand, open-field, full sun trials at a nursery near Vernon, Tex., during which the plants were supplemented with fertilizer and water as needed. These plants are natural habit and were not treated with plant growth regulators and they were not pinched at any time in the growth year. '15719 GRW' has not been observed under all possible environments, and certain characteristics may vary slightly under different environmental conditions. Color references are to The Royal Horticultural Society Colour Chart of The Royal Horticultural Society of London (R.H.S.), 2001 ($4^{th}$ edition).

Propagation:

*Method.*—Stem cuttings.

*Time to initiate roots from stem cuttings after treating cuttings with a commercial rooting hormone.*—About 2 weeks under misting and at an air temperature of 85° C.

*Rooting habit.*—Normal, branching, fleshy, and developing a thick diameter (to about 2.5 cm).

*Root color.*—Pale yellow (between RHS 161D and RHS 162D), depending on soil type.

*Crop time (under normal summer growing conditions and when grown in a 4 L container from a rooted cutting).*—8 to 10 weeks to flower with very good plant vigor.

Plant:

*Plant shape and habit.*—Hardy herbaceous perennial with 6 to 8 thick upright and heavily branched main stems producing an upright spreading mound about 100.0 cm tall and 95.0 cm wide, which is widest about 50 cm above the soil line.

*Primary branches.*—8 to 12 per main stem that protrude at about a 45° angle from horizontal.

*Lateral branches.*—On the middle half of the primary stems.

*Lateral branch size.*—Between 15 cm and 30 cm long (shorter at the upper nodes) and with an average diameter of 8.0 mm at their base.

*Flower location.*—Upper ⅓ of the plant beginning at axillary nodes while still developing at the apex.

*Stem.*—Rounded, glabrous, glaucous; averages about 100.0 cm tall and 3.5 cm diameter at their base.

*Stem color.*—Between brilliant yellowish green (RHS 134C) and strong yellowish green (RHS 135C).

*Internode.*—About 18 nodes per stem below flower and about 32 total, average internode length is about 5.5 cm of unpinched plant, but varies between 3.0 to 6.5 cm and are widest in middle portion of stem.

Foliage:

*Shape.*—Hastate, trilobed with slightly indented margins.

*Texture.*—Adaxial and abaxial matte.

*Leaf blade size.*—To about 16.0 cm long and 8.0 cm wide, larger proximally and becoming smaller in distal portion of stem.

*Foliage color.*—Adaxial and abaxial between vivid yellowish green (RHS 134A) and strong yellowish green (RHS 135C).

*Veins.*—Palmate; adaxial and abaxial veins very pale green (RHS 124D).

*Petiole size (average).*—7.5 cm long and 5.0 mm wide.

*Petiole color.*—Light yellowish green (RHS 135D).

Flowers:

*Buds.*—One day prior to opening about 3.5 cm long and 2.5 cm in diameter, pointed apex and bluntly rounded base, unopened petals wrinkled at veins; and, prior to showing petals, about 3.5 cm long and 2.0 cm in diameter, elongated with acute apex.

*Bud color.*—Exposed petal light violet (RHS 93D) toward apex with vein tinting of strong violet (RHS 93C); and, prior to showing petals, light violet (RHS 93D).

*Epicalyx.*—Entire, smooth, puberulent both surfaces, linear with sharply acute apex and attenuate base, curved around sepals; typically 12 per flower; about 2.5 cm long tapering to base of about 3.0 mm wide.

*Epicalyx color.*—Adaxial and abaxial strong yellowish green (RHS 135C).

*Sepals.*—5, proximal half connate forming campanulate star-shaped calyx; acute apex; margin entire, edentate; puberulent abaxial glabrous adaxial; individually about 3.5 cm long and about 2.5 cm wide at fusion point. From the upper side of the flower, sepals visible as a star shape in the center of the flower.

*Sepal color.*—Abaxial and adaxial color strong yellowish green (RHS 135C).

*Flowers.*—Solitary, about 20 to 30 per main stem without pinching; primarily outwardly facing; average 16 cm across, larger in early part of flowering season; persist for one to two days, depending on temperature; effective for at least 14 weeks beginning early July and lasting into October (north Texas), no detectable fragrance.

*Petals.*—5; glabrous, dull both front and back, adnate to the androecium to form a column, slightly imbricate to about 5% overlapping at widest part (petals about 10% overlapping the next petal to either side). Veins: Palmately veined, primary and secondary veins impressed on front and ribbed on back; veins extend from the eye zone; primary and secondary veins pale purplish pink (RHS 65D). Shape: Rounded. Margins: Entire, edentate, slightly frilled. Apex: Rounded. Base: Short claw-like. Surface: Adaxial and abaxial glabrous, slightly ribbed. Size (average): About 8.0 cm long and about 6.0 cm wide at widest portion (largest in earlier part of flowering season); center dark eye about 4.0 cm diameter. Color: Adaxial and abaxial near very light purplish-blue (RHS 100C) intensifying to very pale purplish blue (RHS 101D) in UV light; center eye dark red (RHS 59A) with an external halo in vivid red (RHS 57A).

*Gynoecium*.—Style: Enclosed in column about 5.0 cm long and 0.5 cm wide at base; column color vivid purplish red (RHS 61C); style protruding from column and split in distal 20.0 mm portion into typically 5 branches, branch diameter 2.0 mm; branch color nearest vivid purplish red (RHS 61C). Stigma: Typically 5; globose, puberulose, about 3.0 mm in diameter; color nearest very pale purple (RHS 69C). Ovary: Superior, about 6.5 mm across at base and 6.0 mm tall; acute apex.

*Androecium*.—Filaments: Numerous, about 180; less than 1.0 mm in diameter and about 5.0 mm long; attached along nearly the entire length of column; color nearest pale purplish pink (RHS 62D). Anthers: Reniform; about 2 mm long and 1 mm wide; nearest light yellow (RHS 163D). Pollen: Numerous, globose, less than 0.1mm long; color light yellow (RHS 163D).

*Pedicel*.—Rounded in cross section, finely puberulent; length from base of sepal to abscission point average 1.5 cm long and 4.0 mm wide, longer on early flowers decreasing in later flowers; color brilliant yellowish green (RHS 135C).

*Peduncle*.—Rounded, puberulent, average about 3.5 to 4.5 cm long from abscission point to stem and 4.0 mm wide, slightly longer on earlier flowers.

*Peduncle color*.—Brilliant yellowish green (RHS 135C).

*Fruit*.—Few, loculicidal capsule; glabrous; globose, occasionally with abruptly acute apex; color between light yellowish brown (RHS 199C) and dark grayish yellow (RHS 199D) when mature.

*Seed*.—Minutely floccose, typically globose; about 3.0 mm in diameter; color between dark grayish reddish brown (RHS 200A) and moderate brown (RHS 200C).

Resistance: The plant grows best with plenty of moisture, but is able to tolerate some drought once established. Other pest and disease resistance beyond that of other hardy perennial *hibiscus* cultivars has not been observed. Hardiness at least from USDA Zone 4 through 9.

Commercial use: Suitable for potted plant culture, landscaping as a specimen or en masse, and especially suited for patios and confined spaces because of the compact habit.

What is claimed is:

1. A new and distinct *Hibiscus* hybrid (L.) plant named '15719 GRW' as shown and described herein.

* * * * *